US011124812B2

(12) United States Patent
Lee et al.

(10) Patent No.: US 11,124,812 B2
(45) Date of Patent: Sep. 21, 2021

(54) PUTRESCINE-PRODUCING MICROORGANISM AND METHOD FOR PRODUCING PUTRESCINE USING THE SAME

(71) Applicant: CJ Cheiljedang Corporation, Seoul (KR)

(72) Inventors: Na Hum Lee, Seoul (KR); Jae Hun Lee, Seoul (KR); Hong Xian Li, Suwon-si (KR); Jun Ok Moon, Yongin-si (KR); Hye Won Um, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/083,193

(22) PCT Filed: Jan. 5, 2017

(86) PCT No.: PCT/KR2017/000134
§ 371 (c)(1),
(2) Date: Sep. 7, 2018

(87) PCT Pub. No.: WO2017/159976
PCT Pub. Date: Sep. 21, 2017

(65) Prior Publication Data
US 2020/0002737 A1    Jan. 2, 2020

(30) Foreign Application Priority Data
Mar. 15, 2016 (KR) .......................... 10-2016-0030898

(51) Int. Cl.
| C12N 1/21 | (2006.01) |
| C12N 9/02 | (2006.01) |
| C12P 13/00 | (2006.01) |
| C12N 1/20 | (2006.01) |
| C12N 9/88 | (2006.01) |
| C12N 15/77 | (2006.01) |

(52) U.S. Cl.
CPC .............. *C12P 13/001* (2013.01); *C12N 1/20* (2013.01); *C12N 9/0008* (2013.01); *C12N 9/88* (2013.01); *C12N 15/77* (2013.01); *C12Y 102/01002* (2013.01); *C12Y 401/01017* (2013.01)

(58) Field of Classification Search
None
See application file for complete search history.

(56) References Cited

U.S. PATENT DOCUMENTS

| 2010/0203599 A1* | 8/2010 | Lee ........................ C12P 13/001 |
| | | 435/128 |
| 2015/0064753 A1* | 3/2015 | Chung ...................... C12P 7/46 |
| | | 435/145 |
| 2016/0222420 A1* | 8/2016 | Botes ................... C12N 9/1096 |

FOREIGN PATENT DOCUMENTS

| EP | 2 977 443 A1 | 1/2016 |
| KR | 10-0620092000 | 8/2006 |
| KR | 10-2009-0107920 | 10/2009 |
| KR | 10-1607741000 | 2/2014 |
| KR | 10-2014-0115244 | 9/2014 |
| KR | 10-2013-0082478 | 2/2015 |
| KR | 10-2015-0028121 | 3/2015 |
| KR | 10-2015-0124398 | 11/2015 |
| WO | WO 2006/065095 A1 | 6/2006 |
| WO | WO 2009/096689 A2 | 8/2009 |
| WO | WO 2014/148743 A1 | 9/2014 |
| WO | WO-2015097020 A1 * | 7/2015 | ............... C12P 7/04 |
| WO | WO 2015/163718 A1 | 10/2015 |

OTHER PUBLICATIONS

Zhou et al., Cell Mol Life Sci 63:2260-2290, 2006 (Year: 2006).*
Kozak, M., Gene 234:187-208, 1999 (Year: 1999).*
Schirwitz et al., Prot. Sci. 16:1146-1156, 2007 (Year: 2007).*
Shen et al., Appl. Environmen. Microbiol. 77:2905-2915, 2011 (Year: 2011).*
Anh Q.D. Nguyen et al., "Fementative Production of the Diamine Putrescine: System Metabolic Engineering of *Corynebacterium glutamicum*", *Metabolites*, 2015, 5, 211-231.
Jens Schneider et al., "Putrescine production by engineered *Corynebacterium glutamicum*", Appl Microbiol Biotechnol, 2010, 88:859-868.
Sabrina Witthoff et al., "*Corynebacterium glutamicum* harbours a molybdenum cofactor-dependent formate dehydrogenase which alleviates growth inhibition in the presence of formate", *Microbiology*, 2012, 158, 2428-2439.
Boris Litsanov et al., "Toward Homosuccinate Fermentation: Metabolic Engineering of *Corynebacterium glutamicum* for Anaerobic Production of Succinate from Glucose and Formate", *Applied and Environmental Microbiology*, May 2012, vol. 78, No. 9.
International Search Report dated Apr. 17, 2017 in connection with PCT International Application No. PCT/KR2017/000134.
Severin A.S. Biochimija. M., GEOTAR-MED, 2004, p. 9.
Jens Schneider et al: "Improving putrescine production by fine-tuning ornithine transcarbamoylase activity using a plasmid addiction system", Applied Microbiology and Biotechnology, Springer, Berlin, DE, vol. 95, No. 1, Feb. 28, 2012, pp. 169-178.

(Continued)

*Primary Examiner* — David Steadman
(74) *Attorney, Agent, or Firm* — Morgan, Lewis & Bockius LLP

(57) ABSTRACT

The present application relates to a putrescine-producing microorganism in which the activity of formate dehydrogenase is increased, and a method for producing putrescine using the same.

6 Claims, 2 Drawing Sheets

Specification includes a Sequence Listing.

(56) References Cited

OTHER PUBLICATIONS

Slusarczyk H et al: "Stabilization of NAD-dependent formate dehydrogenase from Canadia boidinii by site-directed mutagenesis of cysteine residues", European Journal of Biochemistry, Wiley-Blackwell Publishing Ltd, GB, vol. 267, No. 5, Mar. 1, 2000, pp. 1280-1289.
Supplemental European Search Report dated Sep. 2, 2019 in connection with European Patent Application No. 17766877.9.

\* cited by examiner ly produced as a raw material for preparing polyamide. Until now, putrescine has been prepared by chemical methods using petroleum compounds as raw materials, and technologies for producing putrescine by fermentation using genetic engineering technology and fermentation technology are currently being studied.

SEQUENCE LISTING

<160> NUMBER OF SEQ ID NOS: 21

<210> SEQ ID NO 1
<211> LENGTH: 48
<212> TYPE: DNA
<213> ORGANISM: Artificial Sequence
<220> FEATURE:
<223> OTHER INFORMATION: CbFdh primer 1

<400> SEQUENCE: 1
ctacagacca tggctaagat cgttttagtc ttatatgatg ctggtaac        48

<210> SEQ ID NO 2
<211> LENGTH: 46
<212> TYPE: DNA
<213> ORGANISM: Artificial Sequence
<220> FEATURE:
<223> OTHER INFORMATION: CbFdh primer 2

<400> SEQUENCE: 2
tatctcgagt tatttcttat cgtgtttacc gtaagctttg gtaacg          46

<210> SEQ ID NO 3
<211> LENGTH: 20
<212> TYPE: DNA
<213> ORGANISM: Artificial Sequence
<220> FEATURE:
<223> OTHER INFORMATION: T7 promoter primer

<400> SEQUENCE: 3
taatacgact cactataggg                                       20

<210> SEQ ID NO 4
<211> LENGTH: 19
<212> TYPE: DNA
<213> ORGANISM: Artificial Sequence
<220> FEATURE:
<223> OTHER INFORMATION: T7 terminator primer

<400> SEQUENCE: 4
gctagttatt gctcagcgg                                        19

<210> SEQ ID NO 5
<211> LENGTH: 28
<212> TYPE: DNA
<213> ORGANISM: Artificial Sequence
<220> FEATURE:
<223> OTHER INFORMATION: CJ7 promoter primer 1

<400> SEQUENCE: 5
gaaggatcca tagcctaccg atgtagat                              28

<210> SEQ ID NO 6
<211> LENGTH: 31
<212> TYPE: DNA
<213> ORGANISM: Artificial Sequence
<220> FEATURE:
<223> OTHER INFORMATION: CJ7 promoter primer 2

<400> SEQUENCE: 6
aattctagaa gtgtttcctt tcgttgggta c                          31

<210> SEQ ID NO 7
<211> LENGTH: 33
<212> TYPE: DNA
<213> ORGANISM: Artificial Sequence
<220> FEATURE:
<223> OTHER INFORMATION: CbFdh primer 3

<400> SEQUENCE: 7
gaatctagaa tggctaagat cgttttagtc tta                33

<210> SEQ ID NO 8
<211> LENGTH: 34
<212> TYPE: DNA
<213> ORGANISM: Artificial Sequence
<220> FEATURE:
<223> OTHER INFORMATION: CbFdh primer 4

<400> SEQUENCE: 8
aatgtcgact tatttcttat cgtgtttacc gtaa               34

<210> SEQ ID NO 9
<211> LENGTH: 1098
<212> TYPE: DNA
<213> ORGANISM: Artificial Sequence
<220> FEATURE:
<223> OTHER INFORMATION: CbFdh gene

<400> SEQUENCE: 9
atggctaaga tcgttttagt cttatatgat gctggtaagc acgctgctga tgaagaaaaa      60
ttatatggtt gtactgaaaa taaattaggt attgctaatt ggttaaaaga tcaaggtcat     120
gaactaatta ctacttctga taaagaaggt gaaacaagtg aattggataa acatatccca     180
gatgctgata ttatcatcac cactcctttc catcctgctt atatcactaa ggaaagactt     240
gacaaggcta agaacttaaa attagtcgtt gtcgctggtg ttggttctga tcacattgat     300
ttagattata ttaatcaaac aggtaagaaa atctcagtcc tggaagttac aggttctaat     360
gttgtctctg ttgctgaaca cgttgtcatg accatgcttg tcttggttag aaatttcgtt     420
ccagcacatg aacaaattat taaccacgat tgggaggttg ctgctatcgc taaggatgct     480
tacgatatcg aaggtaaaac tatcgctacc attggtgctg gtagaattgg ttacagagtc     540
ttggaaagat tactcccatt taatccaaaa gaattattat actacgatta tcaagcttta     600
ccaaaagaag ctgaagaaaa agttggtgct agaagagttg aaaatattga agaattagtt     660
gctcaagctg atatcgttac agttaatgct ccattacacg caggtacaaa aggtttaatt     720
aataaggaat tattatctaa atttaaaaaa ggtgcttggt tagtcaatac cgcaagaggt     780
gctatttgtg ttgctgaaga tgttgcagca gctttagaat ctggtcaatt aagaggttac     840
ggtggtgatg tttggttccc acaaccagct ccaaaggatc acccatggag agatatgaga     900
aataaatatg gtgctggtaa tgccatgact cctcactact ctggtactac tttagacgct     960
caaacaagat acgctgaagg tactaaaaat attttggaat cattctttac cggtaaattt    1020
gattacagac cacaagatat tatcttatta aatggtgaat acgttaccaa agcttacggt    1080
aaacacgata agaaataa                                                  1098

<210> SEQ ID NO 10
<211> LENGTH: 365
<212> TYPE: PRT
<213> ORGANISM: Artificial Sequence
<220> FEATURE:
<223> OTHER INFORMATION: CbFdh protein

<400> SEQUENCE: 10

Met Ala Lys Ile Val Leu Val Leu Tyr Asp Ala Gly Lys His Ala Ala
1               5                   10                  15

Asp Glu Glu Lys Leu Tyr Gly Cys Thr Glu Asn Lys Leu Gly Ile Ala
            20                  25                  30

Asn Trp Leu Lys Asp Gln Gly His Glu Leu Ile Thr Thr Ser Asp Lys
        35                  40                  45

Glu Gly Glu Thr Ser Glu Leu Asp Lys His Ile Pro Asp Ala Asp Ile
50                  55                  60

Ile Ile Thr Thr Pro Phe His Pro Ala Tyr Ile Thr Lys Glu Arg Leu
65                  70                  75                  80

Asp Lys Ala Lys Asn Leu Lys Leu Val Val Ala Gly Val Gly Ser
                85                  90                  95

Asp His Ile Asp Leu Asp Tyr Ile Asn Gln Thr Gly Lys Lys Ile Ser
            100                 105                 110

Val Leu Glu Val Thr Gly Ser Asn Val Val Ser Val Ala Glu His Val
        115                 120                 125

Val Met Thr Met Leu Val Leu Val Arg Asn Phe Val Pro Ala His Glu
130                 135                 140

Gln Ile Ile Asn His Asp Trp Glu Val Ala Ala Ile Ala Lys Asp Ala
145                 150                 155                 160

Tyr Asp Ile Glu Gly Lys Thr Ile Ala Thr Ile Gly Ala Gly Arg Ile
                165                 170                 175

Gly Tyr Arg Val Leu Glu Arg Leu Leu Pro Phe Asn Pro Lys Glu Leu
            180                 185                 190

Leu Tyr Tyr Asp Tyr Gln Ala Leu Pro Lys Glu Ala Glu Lys Val
        195                 200                 205

Gly Ala Arg Arg Val Glu Asn Ile Glu Glu Leu Val Ala Gln Ala Asp
            210                 215                 220

Ile Val Thr Val Asn Ala Pro Leu His Ala Gly Thr Lys Gly Leu Ile
225                 230                 235                 240

Asn Lys Glu Leu Leu Ser Lys Phe Lys Lys Gly Ala Trp Leu Val Asn
                245                 250                 255

Thr Ala Arg Gly Ala Ile Cys Val Ala Glu Asp Val Ala Ala Ala Leu
            260                 265                 270

Glu Ser Gly Gln Leu Arg Gly Tyr Gly Gly Asp Val Trp Phe Pro Gln
        275                 280                 285

Pro Ala Pro Lys Asp His Pro Trp Arg Asp Met Arg Asn Lys Tyr Gly
290                 295                 300

Ala Gly Asn Ala Met Thr Pro His Tyr Ser Gly Thr Thr Leu Asp Ala
305                 310                 315                 320

Gln Thr Arg Tyr Ala Glu Gly Thr Lys Asn Ile Leu Glu Ser Phe Phe
                325                 330                 335

Thr Gly Lys Phe Asp Tyr Arg Pro Gln Asp Ile Ile Leu Leu Asn Gly
            340                 345                 350

Glu Tyr Val Thr Lys Ala Tyr Gly Lys His Asp Lys Lys
        355                 360                 365

<210> SEQ ID NO 11
<211> LENGTH: 319
<212> TYPE: PRT
<213> ORGANISM: Artificial Sequence
<220> FEATURE:
<223> OTHER INFORMATION: Ornithine carbamoyl transferase (argF)

<400> SEQUENCE: 11

Met Thr Ser Gln Pro Gln Val Arg His Phe Leu Ala Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Thr Asp Ser Leu Asp Glu
210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
290                 295                 300

Ala Gln Lys Ala Leu Leu Val Trp Leu Leu Ala Asn Gln Pro Arg
305                 310                 315

<210> SEQ ID NO 12
<211> LENGTH: 533
<212> TYPE: PRT
<213> ORGANISM: Artificial Sequence
<220> FEATURE:
<223> OTHER INFORMATION: Glutamate exporter

<400> SEQUENCE: 12

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
50                  55                  60

```
Phe Ala Gly Val Gly Val Tyr Ile Ala Gln Ile Val Ala Phe Phe Met
 65                  70                  75                  80
Leu Ala Val Ser Ala Met Gln Ala Phe Gly Phe Ser Leu Ala Gly Ala
                 85                  90                  95
Ala Ile Pro Ala Thr Ile Ala Ser Ala Ala Ile Gly Leu Gly Ala Gln
            100                 105                 110
Ser Ile Val Ala Asp Phe Leu Ala Gly Phe Phe Ile Leu Thr Glu Lys
            115                 120                 125
Gln Phe Gly Val Gly Asp Trp Val Arg Phe Glu Gly Asn Gly Ile Val
            130                 135                 140
Val Glu Gly Thr Val Ile Glu Ile Thr Met Arg Ala Thr Lys Ile Arg
145                 150                 155                 160
Thr Ile Ala Gln Glu Thr Val Ile Ile Pro Asn Ser Thr Ala Lys Val
                165                 170                 175
Cys Ile Asn Asn Ser Asn Asn Trp Ser Arg Ala Val Val Ile Pro
                180                 185                 190
Ile Pro Met Leu Gly Ser Glu Asn Ile Thr Asp Val Ile Ala Arg Ser
                195                 200                 205
Glu Ala Ala Thr Arg Arg Ala Leu Gly Gln Gly Lys Ile Ala Pro Glu
210                 215                 220
Ile Leu Gly Glu Leu Asp Val His Pro Ala Thr Glu Val Thr Pro Pro
225                 230                 235                 240
Thr Val Val Gly Met Pro Trp Met Val Thr Met Arg Phe Leu Val Gln
                245                 250                 255
Val Thr Ala Gly Asn Gln Trp Leu Val Glu Arg Ala Ile Arg Thr Glu
                260                 265                 270
Ile Ile Ser Glu Phe Trp Glu Glu Tyr Gly Ser Ala Thr Thr Thr Ser
                275                 280                 285
Gly Thr Leu Ile Asp Ser Leu His Val Glu His Glu Pro Lys Thr
                290                 295                 300
Ser Leu Ile Asp Ala Ser Pro Gln Ala Leu Lys Glu Pro Lys Pro Glu
305                 310                 315                 320
Ala Ala Ala Thr Val Ala Ser Leu Ala Ala Ser Ser Asn Asp Asp Ala
                325                 330                 335
Asp Asn Ala Asp Ala Ser Val Ile Asn Ala Gly Asn Pro Glu Lys Glu
                340                 345                 350
Leu Asp Ser Asp Val Leu Glu Gln Glu Leu Ser Ser Glu Glu Pro Glu
                355                 360                 365
Glu Thr Ala Lys Pro Asp His Ser Leu Arg Gly Phe Phe Arg Thr Asp
                370                 375                 380
Tyr Tyr Pro Asn Arg Trp Gln Lys Ile Leu Ser Phe Gly Gly Arg Val
385                 390                 395                 400
Arg Met Ser Thr Ser Leu Leu Leu Gly Ala Leu Leu Leu Ser Leu
                405                 410                 415
Phe Lys Val Met Thr Val Glu Pro Ser Glu Asn Trp Gln Asn Ser Ser
                420                 425                 430
Gly Trp Leu Ser Pro Ser Thr Ala Thr Ser Thr Ala Val Thr Thr Ser
                435                 440                 445
Glu Thr Ser Ala Pro Val Ser Thr Pro Ser Met Thr Val Pro Thr Thr
                450                 455                 460
Val Glu Glu Thr Pro Thr Met Glu Ser Asn Val Glu Thr Gln Gln Glu
465                 470                 475                 480
```

Thr Ser Thr Pro Ala Thr Ala Thr Pro Gln Arg Ala Asp Thr Ile Glu
            485             490                 495

Pro Thr Glu Glu Ala Thr Ser Gln Glu Glu Thr Thr Ala Ser Gln Thr
            500             505                 510

Gln Ser Pro Ala Val Glu Ala Pro Thr Ala Val Gln Glu Thr Val Ala
            515             520                 525

Pro Thr Ser Thr Pro
            530

<210> SEQ ID NO 13
<211> LENGTH: 711
<212> TYPE: PRT
<213> ORGANISM: Artificial Sequence
<220> FEATURE:
<223> OTHER INFORMATION: Ornithine decarboxylase (ODC)

<400> SEQUENCE: 13

Met Lys Ser Met Asn Ile Ala Ala Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

```
Tyr Ile Leu Phe Asp Ser Ala Trp Val Gly Tyr Glu Gln Phe Ile Pro
305                 310                 315                 320

Met Met Ala Asp Ser Ser Pro Leu Leu Glu Leu Asn Glu Asn Asp
            325                 330                 335

Pro Gly Ile Phe Val Thr Gln Ser Val His Lys Gln Gln Ala Gly Phe
                340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
                420                 425                 430

Leu Phe Arg Pro Phe Ile Pro Pro Val Val Asp Gly Lys Leu Trp Gln
            435                 440                 445

Asp Tyr Pro Thr Ser Val Leu Ala Ser Asp Arg Arg Phe Phe Ser Phe
450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
    515                 520                 525

Asn Ser Ile Leu Phe Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
            595                 600                 605

Arg Gln Gln Ser Phe Pro Ser Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
            690                 695                 700

Leu Tyr Gly Tyr Val Leu Lys
705                 710
```

```
<210> SEQ ID NO 14
<211> LENGTH: 388
<212> TYPE: PRT
<213> ORGANISM: Artificial Sequence
<220> FEATURE:
<223> OTHER INFORMATION: Acetyl glutamate synthase or Ornithine acetyl
      transferase (ArgJ)

<400> SEQUENCE: 14

Met Ala Glu Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Val Phe Thr Arg Asn
        35                  40                  45

Arg Val Phe Ala Ala Pro Val Lys Val Ser Arg Glu Asn Val Ala Asp
    50                  55                  60

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365
```

Thr Val Arg Thr Thr Asp Leu Ser Phe Ser Tyr Val Glu Ile Asn Ser
        370                 375                 380

Ala Tyr Ser Ser
385

<210> SEQ ID NO 15
<211> LENGTH: 317
<212> TYPE: PRT
<213> ORGANISM: Artificial Sequence
<220> FEATURE:
<223> OTHER INFORMATION: Acetyl glutamate kinase (ArgB)

<400> SEQUENCE: 15

Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Leu Lys Ala
        35                  40                  45

Ala Phe Ala Ala Asp Met Val Phe Leu Arg Thr Val Gly Ala Lys Pro
    50                  55                  60

Val Val Val His Gly Gly Gly Pro Gln Ile Ser Glu Met Leu Asn Arg
65                  70                  75                  80

Val Gly Leu Gln Gly Glu Phe Lys Gly Phe Arg Val Thr Thr Pro
                85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
        115                 120                 125

Ser Gly Glu Asp Ala Gly Leu Phe Thr Ala Gln Lys Arg Met Val Asn
130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ile Gly Ala Glu
        195                 200                 205

Arg Leu Leu Val Leu Thr Asn Val Glu Gly Leu Tyr Thr Asp Trp Pro
210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Asp Lys Asp Gly Glu Leu
305                 310                 315

<210> SEQ ID NO 16
<211> LENGTH: 357

```
<212> TYPE: PRT
<213> ORGANISM: Artificial Sequence
<220> FEATURE:
<223> OTHER INFORMATION: Acetyl gamma glutamyl phosphate reductase
      (ArgC)

<400> SEQUENCE: 16
```

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
        275                 280                 285

Glu Gly Ala Gln Pro Gln Thr Gln Ala Val Leu Gly Ser Asn Met Cys
290                 295                 300

His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
            340                 345                 350

Val Gly Val Ala Pro
        355

```
<210> SEQ ID NO 17
```

```
<211> LENGTH: 391
<212> TYPE: PRT
<213> ORGANISM: Artificial Sequence
<220> FEATURE:
<223> OTHER INFORMATION: Acetyl ornithine aminotransferase (ArgD)

<400> SEQUENCE: 17

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
                20                  25                  30

Asp Gln Gly Asn Val Tyr Ile Asp Leu Leu Ala Gly Ile Ala Val Asn
            35                  40                  45

Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
                100                 105                 110

Ala Asn Glu Ala Ala Phe Lys Ile Ala Arg Leu Thr Gly Arg Ser Arg
            115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
    195                 200                 205

Ala Val Arg Glu Leu Cys Asp Glu Tyr Gly Ile Leu Met Ile Thr Asp
210                 215                 220

Glu Val Gln Thr Gly Val Gly Arg Thr Gly Asp Phe Phe Ala His Gln
225                 230                 235                 240

His Asp Gly Val Val Pro Asp Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
    275                 280                 285

Ala Cys Ala Ala Ala Lys Ala Val Leu Ser Val Val Asp Asp Ala Phe
290                 295                 300

Cys Ala Glu Val Ala Arg Lys Gly Glu Leu Phe Lys Glu Leu Leu Ala
305                 310                 315                 320

Lys Val Asp Gly Val Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
    355                 360                 365

Thr Pro Pro Leu Val Ile Thr Asp Glu Glu Ile Ala Asp Ala Val Lys
370                 375                 380
```

```
Ala Ile Ala Glu Thr Ile Ala
385                 390
```

<210> SEQ ID NO 18
<211> LENGTH: 203
<212> TYPE: PRT
<213> ORGANISM: Artificial Sequence
<220> FEATURE:
<223> OTHER INFORMATION: putrescine acetyltransferase

<400> SEQUENCE: 18

```
Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Asp Gly Thr Pro Glu Leu
            180                 185                 190

Ala Met Trp Lys Pro Pro Ala Met Pro Thr Val
        195                 200
```

<210> SEQ ID NO 19
<211> LENGTH: 203
<212> TYPE: PRT
<213> ORGANISM: Artificial Sequence
<220> FEATURE:
<223> OTHER INFORMATION: putrescine acetyltransferase

<400> SEQUENCE: 19

```
Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Ile Leu Pro Arg
```

```
                        85                  90                  95
Leu Val Ser Ile Phe Gly Ile Lys Ala Ala Gln Val Ala Trp Thr Asp
                100                 105                 110

Leu Ser Ser Ala Arg Phe His Pro Lys Phe Pro His Trp Tyr Leu Tyr
            115                 120                 125

Thr Val Ala Thr Ser Ser Ala Arg Gly Thr Gly Val Gly Ser Ala
        130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Gly Thr Pro Glu Leu
            180                 185                 190

Ala Met Trp Lys Pro Pro Ala Met Pro Thr Val
                195                 200

<210> SEQ ID NO 20
<211> LENGTH: 494
<212> TYPE: PRT
<213> ORGANISM: Artificial Sequence
<220> FEATURE:
<223> OTHER INFORMATION: putrescine exporting protein

<400> SEQUENCE: 20

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
                20                  25                  30

Asp Asn Ser Ile Leu Tyr Thr Ala Leu Pro Leu Leu Arg Glu Gln Leu
            35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
                100                 105                 110

Arg Ala Phe Leu Gly Ile Gly Ala Ala Thr Met Met Pro Ala Thr Leu
            115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
    195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
```

```
                245                 250                 255
Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
            275                 280                 285

Gly Leu Glu Met Thr Thr Ser Gln Arg Phe Gln Leu Ser Val Gly Phe
            290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
                340                 345                 350

Leu Cys Ile Trp Gly Ala Thr His Thr Asp Gly Leu Pro Phe Phe Ile
                355                 360                 365

Ala Gly Leu Phe Phe Met Gly Ala Gly Ala Ser Val Met Ser Val
            370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
                420                 425                 430

Pro Ala Glu Val Ala Asp Asn Phe Ser Ala Gly Val His His Ala Ile
                435                 440                 445

Asp Gly Asp Ala Ala Arg Ala Ser Leu Asp Thr Ala Tyr Ile Asn Val
            450                 455                 460

Leu Ile Ile Ala Leu Val Cys Ala Val Ala Ala Leu Ile Ser Ser
465                 470                 475                 480

Tyr Leu Phe Arg Gly Asn Pro Lys Gly Ala Asn Asn Ala His
                485                 490

<210> SEQ ID NO 21
<211> LENGTH: 494
<212> TYPE: PRT
<213> ORGANISM: Artificial Sequence
<220> FEATURE:
<223> OTHER INFORMATION: putrescine exporting protein

<400> SEQUENCE: 21

Met Ile Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
                20                  25                  30

Asp Asn Ser Ile Leu Tyr Thr Ala Leu Pro Leu Leu Arg Glu Gln Leu
            35                  40                  45

Ala Ala Thr Glu Thr Gln Ala Leu Trp Ile Ile Asn Ala Tyr Pro Leu
        50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
```

```
            115                 120                 125
Ala Leu Ile Arg Ile Thr Phe Glu Asp Glu Arg Arg Asn Thr Ala
        130                 135                 140
Ile Gly Ile Trp Gly Ser Val Ala Ile Leu Gly Ala Ala Gly Pro
145                 150                 155                 160
Ile Ile Gly Gly Ala Leu Leu Glu Phe Phe Trp Trp Gly Ser Val Phe
                165                 170                 175
Leu Ile Asn Val Pro Val Ala Val Ile Ala Leu Ile Ala Thr Leu Phe
                180                 185                 190
Val Ala Pro Ala Asn Ile Ala Asn Pro Ser Lys His Trp Asp Phe Leu
            195                 200                 205
Ser Ser Phe Tyr Ala Leu Leu Thr Leu Ala Gly Leu Ile Val Thr Ile
            210                 215                 220
Lys Glu Ser Val Asn Thr Ala Arg His Leu Pro Leu Leu Val Gly Ala
225                 230                 235                 240
Ile Ile Leu Leu Ile Ile Gly Ala Val Leu Phe Ser Ser Arg Gln Lys
                245                 250                 255
Lys Ile Glu Glu Pro Leu Leu Asp Leu Ser Leu Phe Arg Asn Arg Leu
                260                 265                 270
Phe Leu Gly Gly Val Val Ala Ala Gly Met Ala Met Phe Thr Val Ser
            275                 280                 285
Gly Leu Glu Met Thr Thr Ser Gln Arg Phe Gln Leu Ser Val Gly Phe
            290                 295                 300
Thr Pro Leu Glu Ala Gly Leu Leu Met Ile Pro Ala Ala Leu Gly Ser
305                 310                 315                 320
Phe Pro Met Ser Ile Ile Gly Gly Ala Asn Leu His Arg Trp Gly Phe
                325                 330                 335
Lys Pro Leu Ile Ser Gly Gly Phe Leu Ala Thr Ala Val Gly Ile Ala
                340                 345                 350
Leu Cys Ile Trp Gly Ala Thr His Thr Asp Gly Leu Pro Phe Phe Ile
            355                 360                 365
Ala Gly Leu Phe Phe Met Gly Ala Gly Ala Gly Ser Val Met Ser Val
            370                 375                 380
Ser Ser Thr Ala Ile Ile Gly Ser Ala Pro Val Arg Lys Ala Gly Met
385                 390                 395                 400
Ala Ser Ser Ile Glu Glu Val Ser Tyr Glu Phe Gly Thr Leu Leu Ser
                405                 410                 415
Val Ala Ile Leu Gly Ser Leu Phe Pro Phe Phe Tyr Ser Leu His Ala
                420                 425                 430
Pro Ala Glu Val Ala Asp Asn Phe Ser Ala Gly Val His His Ala Ile
            435                 440                 445
Tyr Gly Asp Ala Ala Arg Ala Ser Leu Asp Thr Ala Tyr Ile Asn Val
            450                 455                 460
Leu Ile Ile Ala Leu Val Cys Ala Val Ala Ala Leu Ile Ser Ser
465                 470                 475                 480
Tyr Leu Phe Arg Gly Asn Pro Lys Gly Ala Asn Asn Ala His
                485                 490
```

PUTRESCINE-PRODUCING MICROORGANISM AND METHOD FOR PRODUCING PUTRESCINE USING THE SAME

CROSS-REFERENCE TO RELATED APPLICATIONS

This application is a § 371 national stage of PCT International Application No. PCT/KR2017/000134, filed Jan. 5, 2017, claiming priority of Korean Patent Application No. 10-2016-0030898, filed Mar. 15, 2016, the contents of each of which are hereby incorporated by reference into the application.

REFERENCE TO A SEQUENCE LISTING

This application incorporates-by-reference nucleotide and/or amino acid sequences which are present in the file named "190213_90646 Substitute Sequence Listing CAS.txt", which is 44.5 kilobytes in size, and which was created Feb. 13, 2019 in the IBM-PC machine format, having an operating system compatibility with MS-Windows, which is contained in the text file filed Feb. 13, 2019 as part of this application.

TECHNICAL FIELD

The present disclosure relates to a putrescine-producing microorganism and a method for producing putrescine using the microorganism.

BACKGROUND ART

Putrescine is known as a raw material for preparing polyamide. Until now, putrescine has been prepared by chemical methods using petroleum compounds as raw materials, and technologies for producing putrescine by fermentation using genetic engineering technology and fermentation technology are currently being studied.

For example, a microorganism capable of producing putrescine is known, in which the metabolic pathway of a microorganism of the genus *Corynebacterium* was manipulated (KR Patent Application Publication No. 2014-0115244, International Publication No. WO 2014-148743).

Meanwhile, formate dehydrogenase is an enzyme that reduces $NAD^+$ (i.e., the second substrate) by catalyzing the oxidation of formic acid, and as a result, it produces NADH and $CO_2$. NADH is known as an important material in the overall metabolism of microorganisms. This is because an increase in NADH can lead to an increase in reducing power in microorganisms, which can be advantageous for the production of a target material.

A method for producing succinic acid and bioalcohol under anaerobic conditions by strengthening NADH using formate dehydrogenase is already known. Succinic acid can be produced by a reductive TCA (reverse TCA) pathway under anaerobic fermentation conditions. The amount of NADH in the reductive TCA pathway is directly related to the production of succinic acid, and two moles of NADH are consumed in the pathway from oxaloacetate to succinic acid. In fact, it has been reported that when succinic acid is produced from glucose under anaerobic conditions, the enhancement of FDH can result in a 20% higher yield of succinic acid (*Appl Environ Microbiol.*, 2012, 78(9): 3325 to 3337). However, unlike succinic acid, NADH is not used as a direct substrate in the biosynthesis pathway of putrescine, and no association has been reported between formate dehydrogenase and putrescine production.

DISCLOSURE

Technical Problem

The present inventors have made efforts to increase putrescine production in a putrescine-producing microorganism, and as a result, they have confirmed that the overexpression of formate dehydrogenase can increase the levels of NADH and ATP in a putrescine-producing microorganism, and thus, the putrescine production can be increased, thereby completing the present disclosure.

Technical Solution

An object of the present disclosure is to provide a putrescine-producing microorganism of the genus *Corynebacterium* in which the activity of formate dehydrogenase (Fdh) is increased compared to that before modification.

Another object of the present disclosure is to provide a method of producing putrescine using the microorganism.

Advantageous Effects of the Invention

The microorganism of the genus *Corynebacterium* with increased putrescine productivity of the present disclosure is modified so that the activity of formate dehydrogenase (FDH) can be increased, which leads to an increase in the production of NADH and ATP. As a result, the microorganism can increase putrescine production and can be effectively used for large-scale production of putrescine.

Figure 1:
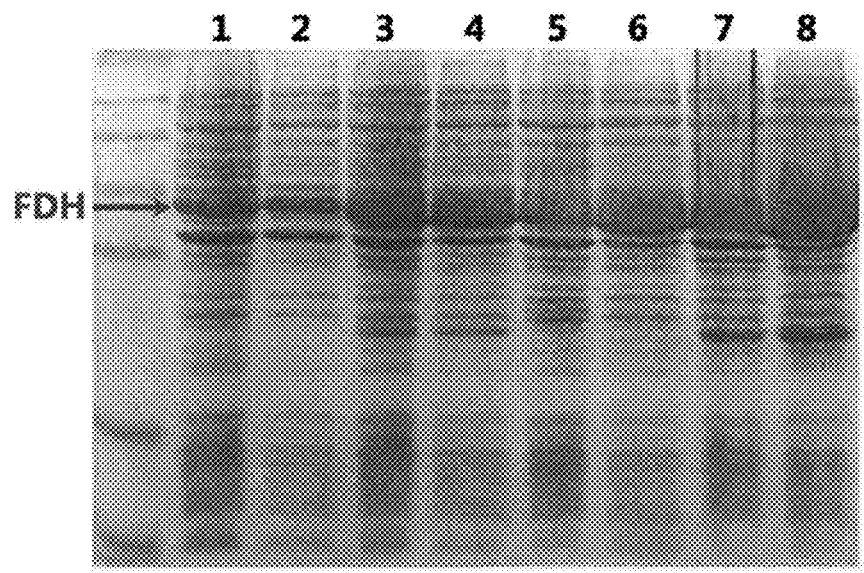
FIG. 1 shows an SDS-PAGE gel image illustrating the results of overexpression of CbFdh using an *Escherichia coli* host, in which Lane 1 represents the result of expression of a protein in a cell lysate which was expressed in *E. coli* BL21 DE3 at 18° C. for 24 hours; Lane 2 represents the result of a soluble protein expressed in *E. coli* BL21 DE3 at 18° C. for 24 hours; Lane 3 represents the result of expression of a protein in a cell lysate which was expressed in *E. coli* BL21 DE3 at 30° C. for 8 hours; Lane 4 represents the result of a soluble protein expressed in *E. coli* BL21 DE3 at 30° C. for 8 hours; Lane 5 represents the result of expression of a protein in a cell lysate which was expressed in *E. coli* Rosetta DE3 at 18° C. for 24 hours; Lane 6 represents the result of a soluble protein expressed in *E. coli* Rosetta DE3 at 18° C. for 24 hours; Lane 7 represents the result of expression of a protein in a cell lysate which was expressed in *E. coli* Rosetta DE3 at 30° C. for 8 hours; and Lane 8 represents the result of a soluble protein expressed in *E. coli* Rosetta DE3 at 30° C. for 8 hours.

*glutamicum* microorganism. CbFdh is a microorganism in which the plasmid pSCEC_CJ7_CbFdh capable of expressing the formate dehydrogenase gene derived from *C. boidinii* is inserted. Formic acid at each concentration of 0 g/L, 2 g/L, and 10 g/L was added to the culture medium, and the changes in the formic acid concentration between the control group and CbFdh were observed.

BEST MODE

To achieve the above objects, in an aspect, the present disclosure provides a putrescine-producing microorganism of the genus *Corynebacterium* in which the activity of formate dehydrogenase is increased.

As used herein, the term "formate dehydrogenase" (hereinafter, "Fdh") collectively refers to an enzyme which catalyzes an oxidation reaction using formic acid as a substrate and thereby reduces $NAD^+$ and produces NADH and $CO_2$.

Since the amino sequence of a given protein showing an activity may vary depending on the species or strain of the microorganism, the origin or sequences of the Fdh are not limited thereto.

Specifically, the Fdh may be derived from *Ceriporiopsis subvermispora, Methylobacterium extorquens, Methylosinus trichosporiuin, Cupriavidus oxalaticus, Candida methylica, Methylotrophic bacterium, Ancylobacter aquaticus, Komagataella pastoris, Mycobacterium vaccae, Arabidopsis thaliana*, etc. and may be derived from *Corynebacterium glutamicum* (Microbiology (2012), 158, 2428 to 2439), which was recently disclosed. Specifically, the Fdh may be derived from *Candida boidinii*, but the origin of the Fdh is not limited thereto.

Additionally, in the present disclosure, the Fdh may include without limitation any protein that has the amino acid sequence of SEQ ID NO: 10, or any protein which, being a protein substantially having the activity of the Fdh, has an amino acid sequence having a homology to the amino acid sequence of SEQ ID NO: 10 of at least 70%, specifically at least 80%, more specifically at least 90%, even more specifically at least 95%, and most specifically at least 99%.

It is apparent that any amino acid sequence which is the same as that of SEQ ID NO: 10 and has a biological activity substantially the same as or equivalent to the protein of SEQ ID NO: 10 can belong to the scope of the present disclosure, even if the amino acid sequence has a partial deletion, modification, substitution, or addition.

The polynucleotide encoding the Fdh of the present disclosure may include a polynucleotide which has a sequence homology to the amino acid sequence of SEQ ID NO: 10 of at least 70%, specifically at least 80%, more specifically at least 90%, even more specifically at least 95%, and most specifically at least 99%, as long as the polynucleotide has an activity similar to that of the Fdh. For example, the polynucleotide may include the nucleotide sequence of SEQ ID NO: 9.

Additionally, the polynucleotide encoding the Fdh of the present disclosure can be hybridized with the nucleotide sequence of SEQ ID NO: 9 or a probe derived from the nucleotide sequence of SEQ ID NO: 9 under stringent conditions, and it may be a modified form encoding the Fdh that functions normally.

As used herein, the term "homology" refers to a degree of identity to a given amino acid Sequence or nucleotide sequence and may be expressed as a percentage. In the present specification, a homologous sequence of the given amino acid sequence or nucleotide sequence having the same or similar activity with the given amino acid sequence or nucleotide sequence may be indicated in terms of "% homology". For example, the homology may be confirmed using standard software for calculating parameters such as score, identity, and similarity, specifically, BLAST 2.0, or by comparing sequences by southern hybridization experiments under defined strict conditions, and the defined stringent hybridization conditions are within the scope of the technology, and may be determined by a method known to one of ordinary skill in the art (e.g., J. Sambrook et al., *Molecular Cloning*, A Laboratory Manual, 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York). As used herein, the term "stringent conditions" refers to conditions that are designed to permit specific hybridization between polynucleotides. For example, these conditions are specifically described in a literature (e.g., J. Sambrook et al., supra).

As used herein, the term "increase of activity" means that the activity is increased compared to the endogenous activity possessed by a microorganism or its activity before modification. The increase of activity may include both introducing an exogenous Fdh and enhancing the activity of the endogenous Fdh. Specifically, the increase of activity may mean that the activity of the Fdh is increased and thereby putrescine-producing ability is increased.

Specifically, the increase of activity in the present disclosure may be performed by the following methods:

(1) increasing the copy number of a polynucleotide encoding the enzyme;

(2) modifying the expression control sequence for increasing the expression of the polynucleotide;

(3) modifying the polynucleotide sequence on the chromosome for enhancing the activity of the enzyme; and (4) modifying the polynucleotide sequence to enhance the enzyme activity by a combination of Methods (1) to (3), etc., but the methods are not limited thereto.

The increase of the copy number of a polynucleotide of Method (1) may be performed in a form where the polynucleotide is operably linked to a vector or by inserting the polynucleotide into the chromosome of a host cell, but the method is not particularly limited thereto. Specifically, the increase of the copy number of a polynucleotide may be performed by introducing into a host cell a vector, to which the polynucleotide encoding the enzyme of the present disclosure is operably linked, that can replicate and function regardless of a host. Alternatively, the increase of the copy number of a polynucleotide may be performed by introducing into a host cell a vector, to which the polynucleotide is operably linked, that can insert the polynucleotide into the chromosome of the host cell, thereby increasing the copy number of the polynucleotide in the chromosome of the host cell.

Additionally, in an aspect, the increase of the copy number may be performed by introducing an exogenous polynucleotide or the polynucleotide in a codon-optimized modified form. The introduction of an exogenous polynucleotide sequence may be performed by introducing into a host cell an exogenous polynucleotide encoding an enzyme that exhibits the same or similar activity to the enzyme. The exogenous polynucleotide may be used without limitation regardless of its origin or sequence as long as it exhibits the same or similar activity to the above enzyme. Additionally, for the optimized transcription and translation of the exogenous polynucleotide in a host cell, its codon may be optimized and introduced into a host cell. The introduction may be performed by one of ordinary skill in the art by selecting a suitable transformation method known in the art, and the expression of the introduced polynucleotide in the host cell can produce the enzyme, thereby increasing its activity.

Then, the modification of the expression control sequence for increasing the expression of a polynucleotide of Method (2) may be performed by inducing a modification of the expression control sequence by deletion, insertion, non-conservative or conservative substitution, or a combination thereof to further enhance the activity of the expression control sequence; or by substituting with a nucleic acid sequence having much stronger activity, although the method is not particularly limited thereto. The expression control sequence may include a promoter, an operator sequence, a sequence encoding a ribosome-binding region, sequences controlling the termination of transcription and translation, etc., but the expression control sequence is not particularly limited thereto.

Specifically, instead of the original promoter, a strong heterologous promoter may be linked upstream of a unit for the polynucleotide expression, and examples of the strong promoter may include CJ7 promoter, lysCP1 promoter, EF-Tu promoter, groEL promoter, aceA promoter, aceB promoter, etc. More specifically, a *Corynebacterium*-derived promoter (e.g., lysCP1 promoter: WO 2009/096689) or CJ7 promoter (Korean Patent No. 10-0620092 and International Publication No. WO 2006/065095) may be operably linked to the unit for the polynucleotide expression so as to increase the expression rate of the polynucleotide encoding the enzyme, but the promoter is not limited thereto.

Furthermore, the modification of the polynucleotide sequence on the chromosome of Method (3) may be performed by inducing a mutation on the expression control sequence by deletion, insertion, non-conservative or conservative substitution of the polynucleotide sequence, or a combination thereof, or by replacing the sequence with a polynucleotide sequence modified to have a further enhanced activity, but the method is not particularly limited thereto.

Finally, Method (4), which relates to modification for enhancing the enzyme activity by a combination of Methods (1) to (3), may be performed by applying a combination of at least one method among the following methods: increasing the copy number of the polynucleotide encoding the enzyme, modifying the expression control sequence to increase the expression of the polynucleotide, modifying the polynucleotide sequence on the chromosome, and modifying an exogenous polynucleotide exhibiting the activity of the enzyme or a codon-optimized modified polynucleotide thereof.

As used herein, the term "vector" refers to a DNA construct including the nucleotide sequence of the polynucleotide encoding a target protein, in which the target protein is operably linked to a suitable control sequence so that it can be expressed in an appropriate host. The control sequence includes a promoter capable of initiating transcription, any operator sequence for the control of the transcription, a sequence encoding an appropriate mRNA ribosome-binding domain, and a sequence controlling the termination of transcription and translation. The vector, after being transformed into a suitable host cell, may be replicated or function irrespective of the host genome, or may be integrated into the host genome itself.

The vector used in the present disclosure may not be particularly limited as long as the vector is able to replicate in a host cell, and any vector known in the art may be used. Examples of the vector may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used; and as a plasmid vector, those based on pBR, pUC, pBluescriptII, pGEM, pTZ, pCL, pET, etc. may be used, and specifically, pDZ, pACYC177, pACYC184, pCL, pECCG117, pUC19, pBR322, pMW118, pCC1BAC, etc. may be used.

In an embodiment, a polynucleotide encoding a target protein in the chromosome may be replaced with a modified polynucleotide through a vector for chromosomal insertion. The insertion of the polynucleotide into the chromosome may be performed by any method known in the art (e.g., homologous recombination), but the method is not limited thereto.

As used herein, the term "transformation" refers to a process of introducing into a host cell a vector including a polynucleotide encoding a target protein, thereby enabling the expression of the protein encoded by the polynucleotide in the host cell. For the transformed polynucleotide, it does not matter whether the transformed polynucleotide is inserted into the chromosome of a host cell and located therein or located outside the chromosome, as long as it can be expressed in the host cell, and both cases are included. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all essential elements required for self-expression. The expression cassette may conventionally include a promoter operably linked to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably linked to a sequence essential for its expression in the host cell, but the polynucleotide is not limited thereto.

Additionally, as used herein, the term "operably linked" refers to a functional linkage between a promoter sequence, which initiates and mediates the transcription of the polynucleotide encoding the target protein of the present disclosure, and the above gene sequence.

As used herein, the term "putrescine-producing microorganism" or "microorganism having putrescine productivity" refers to a microorganism naturally having a putrescine-producing ability or a microorganism, in which a putrescine-producing ability is provided to its parent strain having no putrescine-producing ability.

The putrescine-producing microorganism may be a microorganism having increased productivity of ornithine (i.e., a raw material for the biosynthesis of putrescine), in which the microorganism is modified to have higher activities of acetylglutamate synthase, converting glutamate to N-acetylglutamate, or ornithine acetyltransferase (ArgJ), converting acetyl ornithine to ornithine, acetylglutamate kinase (ArgB), converting acetyl glutamate to N-acetylglutamyl phosphate, acetyl gamma glutamyl phosphate reductase (ArgC), converting acetyl glutamyl phosphate to N-acetylglutamate semialdehyde, or acetylornithine aminotransferase (ArgD), converting acetylglutamate semialdehyde to N-acetylornithine, compared to their endogenous activities, in order to enhance the biosynthesis pathway from glutamate to ornithine glutamate, but is not particularly limited thereto.

Additionally, the microorganism may be a microorganism which is modified to inactivate endogenous activity of ornithine carbamoyltransferase (ArgF), involved in the synthesis of arginine from ornithine, a protein exhibiting the activity of a glutamate exporter, and/or acetyltransferase, which acetylates putrescine, and/or is modified to introduce the activity of ornithine decarboxylase (ODC).

In particular, the ornithine carbamoyltransferase (ArgF), a protein exhibiting the activity of a glutamate exporter, ornithine decarboxylase (ODC), ornithine acetyltransferase (ArgJ), acetylglutamate kinase (ArgB), acetyl gamma glutamyl phosphate reductase (ArgC), and acetylornithine aminotransferase (ArgD) may specifically include an amino acid sequence represented by each of SEQ ID NOS: 11, 12, 13, 14, 15, 16, and 17, or an amino acid sequence having a homology to the above sequences of at least 70%, specifically at least 80%, more specifically at least 90%, even more specifically at least 95%, and most specifically at least 99%, but the amino acid sequences are not particularly limited thereto.

Additionally, the acetyltransferase that acetylates putrescine may specifically include an amino acid sequence represented by SEQ ID NO: 18 or 19 or an amino acid sequence having a homology to the above sequences of at least 70%, specifically at least 80%, more specifically at least 90%, even more specifically at least 95%, and most specifically at least 99%, but the amino acid sequences are not particularly limited thereto.

Additionally, the microorganism may be one in which the activity of the protein exhibiting putrescine export is increased compared to its endogenous activity, but the microorganism is not limited thereto. The protein exhibiting the activity of putrescine export may include an amino acid sequence represented by SEQ ID NO: 20 or 21, and an amino acid sequence having a homology to the above sequences of at least 70%, specifically at least 80%, more specifically at least 90%, even more specifically at least 95%, and most specifically at least 99%, but the amino acid sequences are not particularly limited thereto.

Meanwhile, the microorganism of the present disclosure may be a microorganism having putrescine productivity and it may include prokaryotic microorganisms expressing the Fdh protein (e.g., the microorganisms of the genus *Escherichia, Shigella, Citrobacter, Salmonella, Enterobacter, Yersinia, Klebsiella, Erwinia, Corynebacterium, Brevibacterium, Lactobacillus, Selenomanas, Vibrio, Pseudomonas, Streptomyces, Arcanobacterium, Alcaligenes,* etc.). Specifically, the microorganism of the present disclosure may be a microorganism of genus *Corynebacterium* or genus *Escherichia,* and more specifically *Corynebacterium glutamicum,* but the microorganism is not limited thereto.

In another aspect, the present disclosure provides the use of the *Corynebacterium* microorganism for producing putrescine. The *Corynebacterium* microorganism may be a microorganism in which the activity of formate dehydrogenase (Fdh) is increased compared to that before its modification, and the use may be to produce putrescine.

In still another aspect, the present disclosure provides a method of producing putrescine, which includes (a) culturing a putrescine-producing microorganism of the genus *Corynebacterium* in which the activity of formate dehydrogenase (Fdh) is increased in a medium; and (b) recovering putrescine from the microorganism or the cultured medium obtained in step (a).

The explanations of formate dehydrogenase and the microorganism with enhanced putrescine productivity are the same as described above.

In the above method, culturing a microorganism of the genus *Corynebacterium* may be performed by a known batch culture, continuous culture, fed-batch culture, etc., but the method is not particularly limited thereto. In particular, for the culture conditions, an appropriate pH (e.g., a pH of 5 to 9, specifically a pH of 6 to 8, and most specifically a pH of 6.8) may be adjusted using a basic compound (e.g., sodium hydroxide, potassium hydroxide, or ammonia) or an acidic compound (e.g., phosphoric acid or sulfuric acid), but the pH adjustment is not particularly limited thereto. Additionally, oxygen or an oxygen-containing gas mixture may be introduced into the culture to maintain aerobic conditions. The temperature of the culture may be maintained at 20° C. to 45° C., specifically, 25° C. to 40° C., and may be cultured for 10 hours to 160 hours, but the cultivation conditions are not limited thereto. The produced putrescine may be secreted into the medium or may remain in the cells.

Additionally, as a carbon source for a culture medium used, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used alone or in combination, but the carbon source is not limited thereto. As a nitrogen source, nitrogen-containing organic compounds (e.g., peptone, yeast extract, meat juice, malt extract, corn steep liquor, soybean meal powder, and urea), inorganic compounds (e.g., ammonium sulfate, ammonium chloride, ammonium phosphate, ammonium carbonate, and ammonium nitrate), etc. may be used alone or in combination, but the nitrogen source is not limited thereto. As a phosphorous source, potassium dihydrogen phosphate, dipotassium hydrogen phosphate, sodium-containing salts corresponding thereto, etc. may be used alone or in combination, but the phosphorous source is not limited thereto. Additionally, essential growth-promoting materials such as metal salts (e.g., magnesium sulfate and iron sulfate), amino acids, and vitamins may be contained in the culture medium.

With regard to recovery of the putrescine produced during the cultivation of the present disclosure, desired amino acids may be collected from the culture broth by a suitable method known in the art (e.g., centrifugation, filtration, anion exchange chromatography, crystallization, HPLC, etc.), and the putrescine may be recovered from the cultured medium or microorganism using a suitable method known in the art.

DETAILED DESCRIPTION OF THE INVENTION

Hereinafter, the present disclosure will be described in more detail with reference to the following Examples. However, these Examples are for illustrative purposes only and the scope of the invention is not limited by these Examples.

Example 1: Expression of CbFdh in *E. coli* and Evaluation of Reactivity

1) Expression of CbFdh Gene in *E. coli*

For the overexpression of *Candida boidinii* formate dehydrogenase (CbFdh) in *E. coli, Candida boidinii* KCTC17776 strain was cultured and its genomic DNA was obtained. The formate dehydrogenase gene (CbFdh) (SEQ ID NO: 9) was inserted into pET28a vector using primers of SEQ ID NOS: 1 and 2.

Specifically, PCR was performed under the following conditions: 30 cycles, each consisting of denaturation at 95° C. for 30 seconds, annealing at 55° C. for 30 seconds, and extension at 72° C. for 1 minute. The PCR product was electrophoresed on 1.0% agarose gel and a 1.1 kb band was eluted and purified. A sample containing the purified PCR product and a pET28a vector solution was treated with restriction enzymes, NcoI and XhoI, at 37° C. for 4 hours, electrophoresed on 1.5% agarose gel, and the nucleic acid fragments with a size of the CbFdh and the vector were each cut out, and the purified nucleic acid fragments were obtained using the Gel prep kit (GeneAll, Korea). The CbFdh fragment and the vector fragment, in an amount of 1 mg each, were ligated using T4 ligase and electroporated into E. coli DH5α strain at 2,500 V. After the electroporation, the recovered strain was plated on LB plate medium containing spectinomycin (50 μg/L), cultured overnight at 37° C. for one day, and the resistant strains were selected therefrom. The recovered strain was plated on LB plate medium containing kanamycin (50 μg/L), cultured overnight at 37° C. for one day, and the resistant strains were selected. The selected strain was subjected to PCR under the same conditions as described above using T7 promoter and primers of SEQ ID NOS: 3 and 4 of the terminator sequence, electrophoresed on 1.0% agarose gel, and the insertion of CbFdh was confirmed by observing a 1.3 kb band.

The strain, in which the insertion of CbFdh was confirmed, was cultured in LB medium (3 mL) at 37° C. for 12 hours after adding ampicillin (50 mg/mL) thereto. The cultured strain was added into LB medium (50 mL) containing an antibiotic and cultured at 37° C. When the absorbance at 600 nm reached 0.8, 0.2 mM IPTG was added thereto and expression was induced under various temperature/time conditions. The cultured strain was washed and the cells were lysed using a sonicator. After the cell lysis, CbFdh (41 kDa, SEQ ID NO: 10) was confirmed to be overexpressed through the results of SDS-PAGE gel electrophoresis (FIG. 1).

2) Evaluation of Activity of Expressed CbFdh Gene

For the evaluation of the activity of CbFdh, 100 mM phosphate buffer (pH 7.2) was used as a reaction buffer. The solution which was prepared by adding 10 mM $NAD^+$ and 0.1% sodium formate to the buffer was used as the control group. Meanwhile, the lysate of the cells, in which the overexpression of CbFdh was confirmed in Example 1-1, was added to the control group to a concentration of 10% and the activity of CbFdh was evaluated. The changes in value of the reaction solution were confirmed at the wavelength of 339 nm using a 96-well plate reader. The light at the wavelength of 340 nm is known to be selectively absorbed by NADH.

Figure 2:
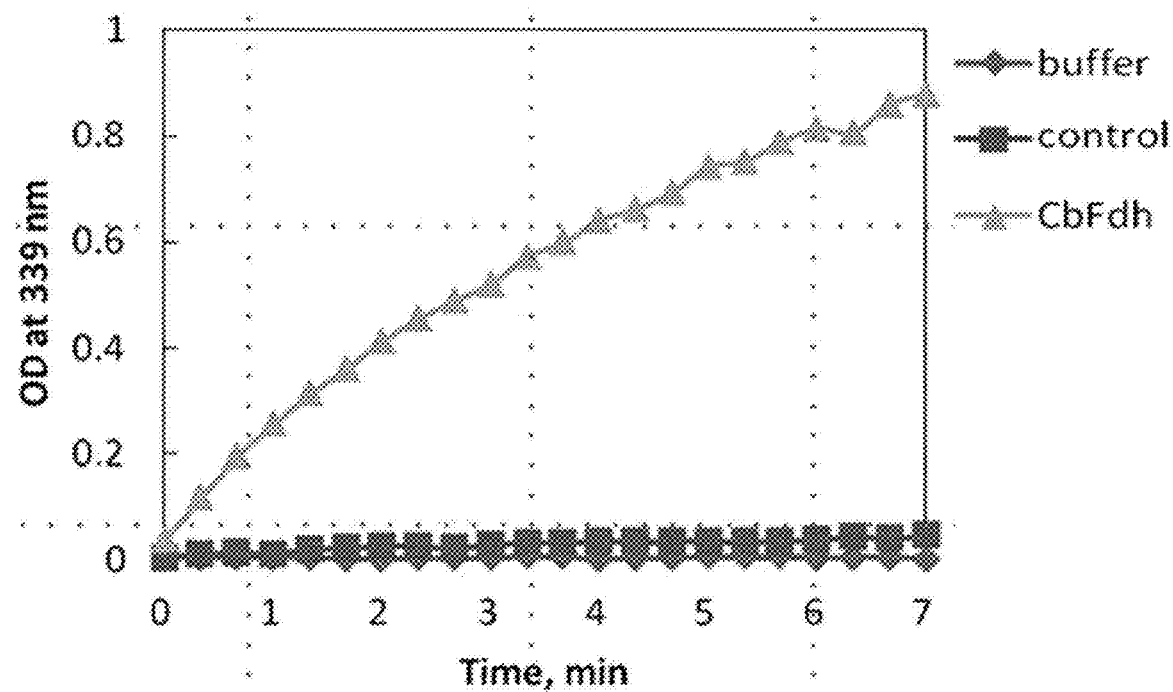
FIG. 2 shows a graph illustrating the amount of NADH produced over time. The buffer used was 100 mM phosphate buffer (pH 7.2) and the control group used was a reaction sample excluding the soluble protein. CbFdh is a reaction sample containing 10% of a soluble protein, which is formate dehydrogenase overexpressed at 30° C. using *E. coli* BL21 DE3. In the case of CbFdh, it was confirmed that the amount of NADH (i.e., a reactant of CbFdh) continued to increase over time.

As a result, it was confirmed that NADH was continuously produced for several minutes (FIG. 2). Through this Example, it was evaluated that CbFdh can be overexpressed in E. coli and that the expressed protein has its unique activity.

Example 2: Preparation of Corynebacterium Microorganism Expressing CbFdh

Then, an attempt was made to confirm whether the putrescine-producing ability can be increased by enhancing the function of CbFdh to a putrescine-producing microorganism of the genus Corynebacterium. To express CbFdh in the microorganism of the genus Corynebacterium and confirm its activity, CJ7 promoter (KCCM10617, KR Pat. No. 10-0620092) was introduced in a region upstream of the initiation codon of the CbFdh gene.

First, PCR was performed using the genomic DNA of Corynebacterium glutamicum ATCC13032 as a template along with a pair of primers of SEQ ID NOS: 5 and 6 so as to obtain the gene including the CJ7 promoter sequence. PCR was performed under the following conditions: 30 cycles, each consisting of denaturation at 95° C. for 30 seconds, annealing at 55° C. for 30 seconds, and extension at 72° C. for 30 seconds. The electrophoresis was performed on 1.5% agarose gel and the presence of a nucleic acid as the PCR product with a size of 400 base pairs (bp) was confirmed. A purified nucleic acid fragment of CJ7 promoter was secured from the obtained PCR product using the PCR prep kit (GeneAll, Korea). A sample containing the purified nucleic acid fragment of CJ7 promoter and a pSCEC vector solution was treated with restriction enzymes, BamHI and XbaI, at 37° C. for 4 hours, electrophoresed on 1.5% agarose gel, and the nucleic acid fragments with a size of 400 bp were cut out, and the fragment of CJ7 promoter and nucleic acid fragments of the pSCEC vector were obtained using the Gel prep kit (GeneAll, Korea). The fragment of CJ7 promoter and the pSCEC vector, in an amount of 1 mg each, were ligated using T4 ligase and electroporated into E. coli DH5a strain at 2,500 V. After the electroporation, the recovered strain was plated on LB plate medium containing spectinomycin (50 μg/L), cultured overnight at 37° C. for one day, and 18 different types of resistant strains were selected therefrom. The selected 18 different types of strains were subjected to colony PCR using the primers of SEQ ID NOS: 5 and 6, and the presence of a PCR product with a 400 bp size was confirmed. From the results of the colony PCR, the preparation of pSCEC_CJ7 having CJ7 promoter was confirmed.

In the same conditions to obtain the PCR product of CbFdh as in Example 1, the PCR product of CbFdh that can be inserted into pSCEC_CJ7 using the primers of SEQ ID NOS: 7 and 8 was obtained. The pSCEC_CJ7, which was treated with restriction enzymes (XbaI and SalI) and the PCR product of CbFdh were ligated and then inserted into E. coli DH5a. The pSCEC_CJ7_CbFdh was obtained from the selected strains and electroporated into putrescine-producing microorganisms of the genus Corynebacterium (i.e., KCCM11240P (KR Pat. Application Publication No. 2013-0082478) and KCCM11401P (KR Pat. Application Publication No. 2014-0017243)) at 2,500 V.

The strains obtained by electroporation were cultured by plating on BHIS plate medium (brain heart infusion 37 g/L, sorbitol 91 g/L, and agar 2%) containing spectinomycin (50 μg/L) and thereby colonies were formed. The selected strains were cultured in a shaking incubator in CM medium (glucose 10 g/L, polypeptone 10 g/L, yeast extract 5 g/L, beef extract 5 g/L, NaCl 2.5 g/L, and urea 2 g/L (pH 6.8)) containing spectinomycin (50 μg/L) and thereby finally selected. The KCCM11240P strain in which pSCEC_CJ7_CbFdh is inserted was named as KCCM11240P/pSCEC_CJ7_CbFdh (CC04-0081), and the KCCM11240P in which pSCEC_CJ7 is inserted was named as KCCM11240P/pSCEC_CJ7. Likewise, the KCCM11401P strain in which pSCEC_CJ7_CbFdh is inserted was named as KCCM11401P/pSCEC_CJ7_CbFdh, and the KCCM11401P strain \ in which pSCEC_CJ7 is inserted was named as KCCM11401P/pSCEC_CJ7.

Among these, the CC04-0081 strain was deposited at Korean Culture Center of Microorganisms (KCCM), which is an international depositary authority under the Budapest Treaty, on Jan. 8, 2016 (Accession No. KCCM 11798P).

Example 3: Evaluation of CbFdh Activity in *Corynebacterium* Microorganism

Figure 3:
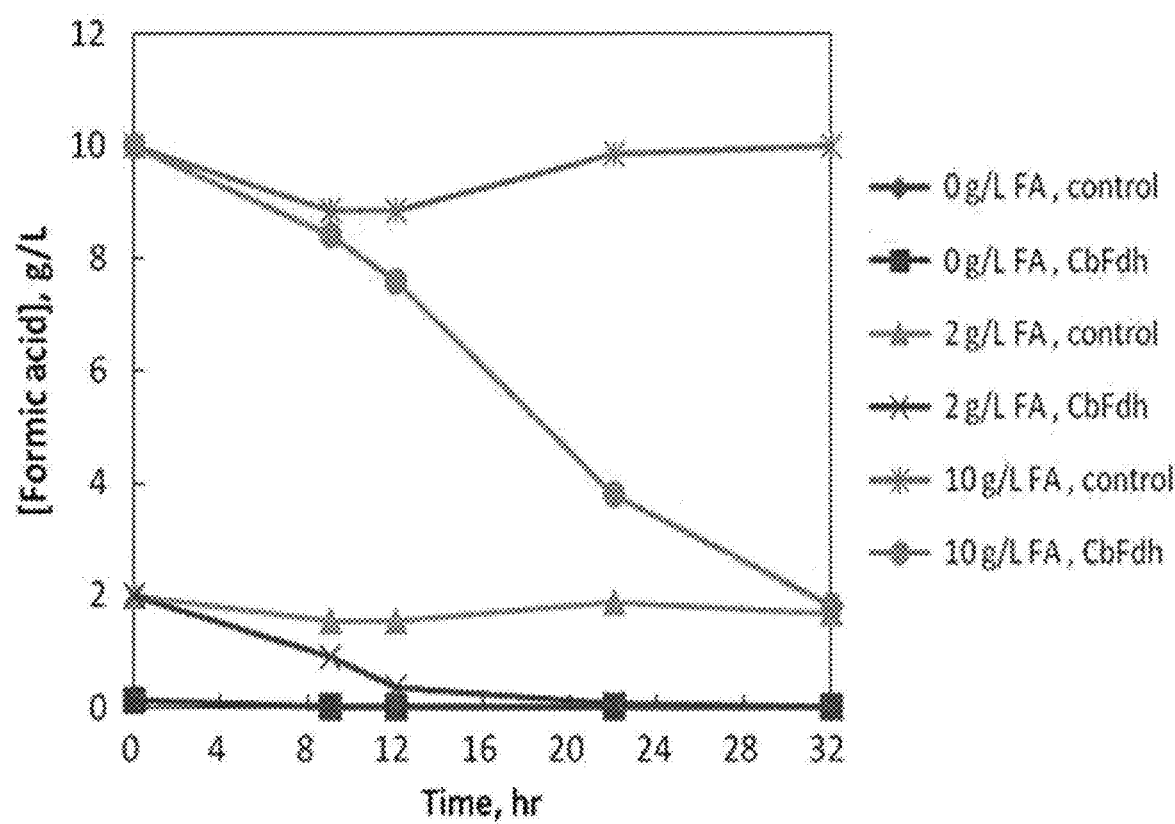
FIG. 3 shows a graph illustrating the concentration of formic acid over time. The control group is a strain in which pSCEC_CJ7 vector was inserted into a *Corynebacterium*

To confirm the activity of formate decarboxylase in a microorganism of the genus *Corynebacterium* where CbFdh is inserted, the changes in formic acid concentration in a medium where formic acid was added were analyzed (FIG. 3). Formic acid at each concentration of 0 g/L, 2 g/L, and 10 g/L was added to a culture broth of a *Corynebacterium* strain where CbFdh activity was enhanced and a culture broth of a *Corynebacterium* strain where an empty vector was inserted. As the strain with enhanced CbFdh activity and the strain with an empty vector, KCCM11240P/pSCEC_CJ7_CbFdh and KCCM11240P/pSCEC_CJ7 were used, respectively.

As a result of the cultivation, it was confirmed that in the case of the strain with an empty vector, formic acid remained in the culture broth when formic acid was added to the culture broth at each concentration of 2 g/L and 10 g/L. In contrast, in the case of the strain with enhanced CbFdh activity, the formic acid added at a concentration of 2 g/L was all decomposed within 24 hours, and additionally, the formic acid added at a concentration of 10 g/L was not all decomposed within 32 hours, but the formic acid level continued to decrease. Comparing with the control group strain at the time point of 32 hours, it was confirmed that about 80% of formic acid was converted.

From the analysis of the changes in the amount of formic acid, it was confirmed that the strain with enhanced CbFdh activity decomposes formic acid. As a result, it was confirmed that the CbFdh introduced to a microorganism of the genus *Corynebacterium* was normally expressed and its function was maintained.

Example 4: Evaluation of Productivity of Putrescine-Producing *Corynebacterium* Microorganism with Enhanced CbFdh Activity Each of the four types of modified *Corynebacterium glutamicum* strains (i.e., KCCM11240P/pSCEC_CJ7_CbFdh, KCCM11240P/pSCEC_CJ7, KCCM11401P/pSCEC_CJ7CbFdh, and KCCM11401P/pSCEC_CJ7) prepared for the evaluation of productivity of putrescine-producing *Corynebacterium* microorganism with enhanced CbFdh activity was spread on CM plate medium (glucose (1%), polypeptone (1%), yeast extract (0.5%), beef extract (0.5%), NaCl (0.25%), urea (0.2%), 50% NaOH (100 μL), spectinomycin (50 μg), agar (2%), pH 6.8, based on 1 L) containing arginine (1 mM), and cultured at 30° C. for 24 hours. A platinum loop of each strain cultured therefrom was inoculated into 25 mL of a titer medium (glucose (8%), soybean protein (0.25%), corn steep solids (0.50%), $(NH_4)_2SO_4$ (4%), $KH_2PO_4$ (0.1%), $MgSO_4 \cdot 7H_2O$ (0.05%), urea (0.15%), biotin (100 μg), thiamine.HCl (3 mg), calcium-pantothenic acid (3 mg), nicotinamide (3 mg), $CaCO_3$ 5%, spectinomycin (50 μg), based on 1 L), and then cultured in a shaking incubator 30° C. at 200 rpm for 98 hours in the case of KCCM11240P/pSCEC_CJ7_CbFdh and KCCM11240P/pSCEC_CJ7 strains, and 104 hours in the case of KCCM11401P/pSCEC_CJ7_CbFdh and KCCM11401P/pSCEC_CJ7 strains.

The concentrations of putrescine produced from each culture product were measured and the results are shown in Table 1 below.

TABLE 1

| Strain | Addition of Formic Acid (g/L) | Putrescine (g/L) |
| --- | --- | --- |
| KCCM11240P/pSCEC_CJ7 | 0 | 12.2 |
| KCCM11240P/pSCEC_CJ7 | 5 | 12.3 |
| KCCM11240P/pSCEC_CJ7_CbFdh | 0 | 13.4 |
| KCCM11240P/pSCEC_CJ7_CbFdh | 5 | 13.1 |
| KCCM11401P/pSCEC_CJ7 | 0 | 11.4 |
| KCCM11401P/pSCEC_CJ7 | 5 | 10.7 |
| KCCM11401P/pSCEC_CJ7_CbFdh | 0 | 12.0 |
| KCCM11401P/pSCEC_CJ7_CbFdh | 5 | 12.0 |

The putrescine concentration in the culture was analyzed by HPLC. As shown in Table 1 above, in the case of the KCCM11240P/pSCEC_CJ7 strain, there was no significant change in the amount of putrescine production according to the presence/absence of formic acid (5 g/L). In contrast, the strain in which KCCM11240P/pSCEC_CJ7_CbFdh was introduced showed an increase in the amount of putrescine production by more than 7% compared to the amount of production by the KCCM11240P/pSCEC_CJ7 strain, regardless of the presence/absence of formic acid (5 g/L). It was confirmed that the amount of putrescine production of the strain in which the Fdh activity was enhanced was increased regardless of the presence/absence of formic acid.

Additionally, in the case of the KCCM11401P/pSCEC_CJ7 strain, which was evaluated in the same medium without the addition of formic acid, the amount of putrescine produced was 11.4 g/L and the KCCM11401P/pSCEC_CJ7 strain cultured in a medium where formic acid. (5 g/L) was added, the yield was decreased by about 6% (10.7 g/L). In contrast, in the case of the KCCM11401P/pSCEC_CJ7_CbFdh strain where the CbFdh activity was enhanced, the same amount of putrescine (12.0 g/L) was produced regardless of the presence/absence of formic acid.

As a result of the analysis of the putrescine produced from the KCCM11401P/pSCEC_CJ7_CbFdh strain and the KCCM11401P/pSCEC_CJ7 strain, it was confirmed that the strain where the CbFdh activity was enhanced showed an increase in putrescine production by at least 5% compared to the KCCM11401P/pSCEC_CJ7 strain. It was confirmed that the strain where the CbFdh activity was enhanced showed an increase in putrescine productivity regardless of the presence/absence of formic acid.

Summarizing the above results, it was confirmed that the strain where formate dehydrogenase (CbFdh) is introduced in a putrescine-producing microorganism showed a further increase in the amount of putrescine production, and this is an effect that appears regardless of the addition of formic acid. Accordingly, it is expected that the present disclosure enables efficient production of putrescine on a large scale.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified *Corynebacterium glutamicum* microorganism producing increased putrescine as compared to an unmodified, wild-type *Corynebacterium glutamicum* microorganism, in which the modified microorganism
   (A) has increased formate dehydrogenase (Fdh) activity as compared to the Fdh activity of the unmodified, wild-type *Corynebacterium glutamicum* microorganism as a result of introducing a polynucleotide encoding Fdh from *Candida boidinii* into the modified microorganism, wherein the amino acid sequence of the Fdh consists of the amino acid sequence of SEQ ID NO: 10, and wherein the polynucleotide encoding the Fdh from *Candida boidinii* comprises the nucleic acid sequence of SEQ ID NO: 9; and
   (B) has ornithine decarboxylase (ODC) activity as a result of introducing a polynucleotide encoding ODC into the modified microorganism.

2. A modified *Corynebacterium glutamicum* microorganism producing increased putrescine as compared to an unmodified, wild-type *Corynebacterium glutamicum* microorganism, in which the modified microorganism
   (A) has increased formate dehydrogenase (Fdh) activity as compared to the Fdh activity of the unmodified, wild-type *Corynebacterium glutamicum* microorganism as a result of introducing a polynucleotide encoding Fdh from *Candida boidinii* into the modified microorganism, wherein the amino acid sequence of the Fdh consists of the amino acid sequence of SEQ ID NO: 10, and wherein the polynucleotide encoding the Fdh from *Candida boidinii* comprises the nucleic acid sequence of SEQ ID NO: 9; and
   (B) has ornithine decarboxylase (ODC) activity as a result of introducing a polynucleotide encoding ODC into the modified microorganism; and
   (C) has increased putrescine export activity as a result of introducing a polynucleotide encoding a polypeptide having putrescine export activity into the modified microorganism.

3. The modified *Corynebacterium glutamicum* microorganism of claim 1, in which the modified microorganism further
   (C) has reduced putrescine acetyltransferase activity as a result of inactivating a putrescine acetyltransferase gene in the modified microorganism.

4. The modified *Corynebacterium glutamicum* microorganism of claim 1, in which the modified microorganism further
   (C) has increased putrescine export activity as a result of introducing a polynucleotide encoding a polypeptide having putrescine export activity into the modified microorganism; and
   (D) has reduced putrescine acetyltransferase activity as a result of inactivating a putrescine acetyltransferase gene in the modified microorganism.

5. A modified *Corynebacterium glutamicum* microorganism transformed by a vector comprising a formate dehydrogenase (Fdh) gene comprising the nucleic acid sequence of SEQ ID NO: 9.

6. The modified *Corynebacterium glutamicum* microorganism of claim 5, wherein the formate dehydrogenase (Fdh) gene consists of the nucleic acid sequence of SEQ ID NO: 9.

* * * * *